(12) United States Patent
Saigh

(10) Patent No.: US 11,497,449 B2
(45) Date of Patent: Nov. 15, 2022

(54) ORAL AND SALIVA BASED EQUINE ID DRUG MONITORING SYSTEM

(71) Applicant: Michael M. Saigh, St. Louis, MO (US)

(72) Inventor: Michael M. Saigh, St. Louis, MO (US)

(73) Assignee: Equine Smartbit, LLC, Clayton, MO (US)

( * ) Notice: Subject to any disclaimer, the term of this patent is extended or adjusted under 35 U.S.C. 154(b) by 595 days.

(21) Appl. No.: 16/130,028

(22) Filed: Sep. 13, 2018

(65) Prior Publication Data

US 2019/0209091 A1 Jul. 11, 2019

Related U.S. Application Data

(63) Continuation-in-part of application No. 15/623,089, filed on Jul. 21, 2017.

(51) Int. Cl.

| | |
|---|---|
| A61B 5/00 | (2006.01) |
| A61B 1/24 | (2006.01) |
| A61B 5/1178 | (2016.01) |
| A61B 5/1455 | (2006.01) |
| A61B 5/01 | (2006.01) |
| A61B 5/0205 | (2006.01) |
| A61B 1/06 | (2006.01) |
| A61B 10/00 | (2006.01) |
| A61B 9/00 | (2006.01) |
| A61C 9/00 | (2006.01) |
| G01N 33/94 | (2006.01) |
| B68B 1/06 | (2006.01) |
| A61B 1/00 | (2006.01) |
| A61B 5/0215 | (2006.01) |
| A61B 5/024 | (2006.01) |

(52) U.S. Cl.
CPC ........ *A61B 5/6895* (2013.01); *A61B 1/00009* (2013.01); *A61B 1/06* (2013.01); *A61B 1/24* (2013.01); *A61B 5/0008* (2013.01); *A61B 5/01* (2013.01); *A61B 5/02055* (2013.01); *A61B 5/1178* (2013.01); *A61B 5/14552* (2013.01); *A61B 5/682* (2013.01); *A61B 5/6846* (2013.01); *A61B 10/0051* (2013.01); *A61C 9/0053* (2013.01); *B68B 1/06* (2013.01); *G01N 33/94* (2013.01); *A61B 5/0215* (2013.01); *A61B 5/02444* (2013.01); *A61B 2503/40* (2013.01)

(58) Field of Classification Search
CPC ....... A61B 5/00; A61B 5/145; A61B 5/14552; A61B 5/682; A61B 5/6895; A61B 5/0002; A61B 2560/0443
See application file for complete search history.

(56) References Cited

U.S. PATENT DOCUMENTS 7,440,788 B2 * 10/2008 Jenkins .............. A61B 5/14552
600/322
9,795,296 B2 * 10/2017 Imran .................... A61B 5/682
(Continued)

*Primary Examiner* — Eric F Winakur
(74) *Attorney, Agent, or Firm* — Polsinelli PC

(57) ABSTRACT

The present disclosure relates to an oral cavity based device, system and toolkit which identifies the human or animal through the unique demarcations oral cavity. These unique demarcations are described as "oralsprint" identifiers (IDs) used to both identify and measure saliva-based biologics and other biometrics through one or more electronic sensors and related technologies for humans and animals to herein as ORAL AND SALIVA BASED EQUINE ID DRUG MONITORING.

15 Claims, 4 Drawing Sheets

(56) References Cited

U.S. PATENT DOCUMENTS

| | | |
|---|---|---|
| 9,872,481 B2 | 1/2018 | Goldfain |
| 2004/0133081 A1 | 7/2004 | Teller |
| 2007/0033068 A1 | 2/2007 | Rao |
| 2007/0106138 A1* | 5/2007 | Beiski .................... A61B 5/682 |
| | | 600/349 |
| 2009/0239710 A1 | 9/2009 | Shemesh |
| 2010/0185398 A1 | 7/2010 | Berns |
| 2011/0165998 A1 | 7/2011 | Lau |
| 2013/0253286 A1* | 9/2013 | Fridman ................ A61B 5/682 |
| | | 600/301 |
| 2014/0275850 A1 | 9/2014 | Venkatraman |
| 2014/0378853 A1 | 12/2014 | McKinney |
| 2015/0185088 A1 | 7/2015 | Rabieirad |
| 2016/0100758 A1 | 4/2016 | Jeong |
| 2016/0135431 A1 | 5/2016 | Sheldon |
| 2016/0136482 A1 | 5/2016 | Askew, Jr. |
| 2016/0165852 A1 | 6/2016 | Goldfain |
| 2016/0165853 A1 | 6/2016 | Goldfain |
| 2016/0173440 A1 | 6/2016 | Stahura |
| 2016/0174099 A1 | 6/2016 | Goldfain |
| 2016/0178392 A1 | 6/2016 | Goldfain |
| 2016/0344740 A1 | 11/2016 | Choi |
| 2017/0086428 A1 | 3/2017 | Horton |
| 2017/0091412 A1 | 3/2017 | Johnson |
| 2017/0108236 A1 | 4/2017 | Guan |
| 2017/0135315 A1 | 5/2017 | Marman |
| 2017/0180959 A1 | 6/2017 | Kim |
| 2017/0334354 A1 | 11/2017 | Hatton |
| 2018/0014512 A1 | 1/2018 | Arabani |
| 2018/0040231 A1 | 2/2018 | DeLuca |
| 2018/0064068 A1 | 3/2018 | McKee |
| 2019/0059325 A1 | 2/2019 | DeLuccia |
| 2019/0133500 A1 | 5/2019 | Basu |

\* cited by examiner

ORAL AND SALIVA BASED EQUINE ID DRUG MONITORING SYSTEM

This application is a provisional application, and it is a continuation-in-part, and claims the benefit of the priority filing date, Jun. 14, 2017, of U.S. patent application Ser. No. 15/623,089, the teachings of which are incorporated herein in their entireties by reference.

STATEMENT REGARDING FEDERALLY SPONSORED RESEARCH OR DEVELOPMENT

Not applicable.

The present disclosure relates to an oral cavity based device, system and toolkit which identifies (IDs) an equine through distinguishing oral and saliva "fingerprints" used for equine drug testing biometrics through one or more electronic sensors and related technologies for humans and animals to herein as ORAL AND SALIVA BASED EQUINE ID AND DRUG MONITORING SYSTEM.

BACKGROUND

Presently illegal drugs are prevalent in equine sports. Equine drug testing is a form of drug testing applied to performance horses in regulated competition. Most common in racehorses, drug tests are also performed on horses in endurance riding and in international competition such as the Olympics and FEI-sanctioned competition. Recent challenges in drug testing include the development of effective regulatory methods for the newer hormonal products such as the various human recombinant erythropoietin products and variants and growth hormones. A high-quality ELISA test for human recombinant erythropoietin is now available, and recently the first Mass Spectral Confirmation method to detect use of human recombinant erythropoietin (rhEPO) in horses or any species was developed.

At the time of this writing, approximately 25 medications are now approved by the Association of Racing Commissioners International (ARCI) for therapeutic use in race horses. This situation has led to the establishment of "thresholds" or "reporting levels," or "decision levels" depending on the semantic preference of individual jurisdictions. These terms apply to the blood concentration of a medication below which it is believed by scientists and racing authorities that the medication has insignificant pharmacological effect. Thresholds (cutoffs) have long been used in human drug testing, however, the concept has been slow to be accepted by horse racing regulators.

Therapeutic medications (or drugs) are properly used to alleviate pain and to allow or promote healing. However, in the sport of horse racing powerful painkilling drugs may be used daily, often in combination with several other potent drugs, to enable injured horses to train and race before their injuries are fully healed. When this happens, the logical result is that additional injury can occur, rapidly accelerating the need for ever more powerful drugs to keep a horse racing. The widespread use of pharmaceuticals is unique to American racing and many believe it puts racehorses at greater risk of crippling injuries and death. Jockeys are also exposed to far greater risk, as medicated horses are much more likely to suffer catastrophic breakdowns during a race sending horses and riders tumbling.

In a series of articles on drugs and racing The New York Times estimates that approximately 24 horses are killed because of injuries incurred during a race each week in America, though the question of how many of these deaths are linked to misuse of medication is undetermined.

For decades, outside scrutiny had been focused on the question of whether horse trainers seek increasing access to pre-race drugs to keep sore horses in training and racing. But in recent years the focus has broadened to include attending veterinarians for racehorses. Experts contend that veterinarians who provide drugs to keep injured horses racing violate veterinary practice laws regarding proper ethics, standards and practices.

Identification of these substances in a horse is viewed with great regulatory concern. Testing for these substances usually proceeds at the highest level of sensitivity possible, so-called "zero-tolerance" testing. Approximately 1000 substances are classified by the Association of Racing Commissioners International (ARCI) Uniform Classification System for Foreign Substances as potentially performance-enhancing in a five-class system. The most complete listing of such substances is found online.

Stimulants—the equine stimulants are amphetamines, as well as the amphetamine-like drugs such as methylphenidate (Ritalin).

Tranquilizers—horses can also be medicated to win by relaxing them, and allowing the horse to run its best possible race or show with an appearance. The widely-used tranquilizer acepromazine, and any number of related or equivalent agents, have been used in this way. Bronchodilators—improves a horse's "wind" by opening its airways using bronchodilators may also improve performance, especially in an animal that is sub-clinically broncho-constricted.

Many horses in competition sanctioned by various national organizations, such as the United States Equestrian Federation in the USA are also tested for improper drug use.

Thousands of illegal drugs are constantly being developed for both the equine industry and human sports.

Presently, there are no effective and foolproof methods of identifying non-evasive drug cheaters in the sports industry. The lure of large purses and salaries for winning athletes and winning thoroughbreds are too great no matter the cost of injury.

Furthermore, the "cat and mouse game" in trying to detect illegal drugs and masking illegal drugs are both ineffective and very costly.

The present invention will help solve drug detection as associated to the identification of human, equine and other animals as described by the following.

SUMMARY OF THE INVENTION

The invention includes both non-invasive continuous monitoring and occasional measurements using saliva gathered from the oral cavity, various irreplaceable biosensor modules and drug and health test strip modules which can be replenished, securely locked and interchange—these new technologies are collectively components of the "smartbit".

The invention uses one or more biosensors. These microprocessors, sensors and electronics are embedded or attached to a mouth retainer, horse-bit, mouth guard, sports guard, one or more teeth, dentures, etc. hereby referred to as a Smartbit ID System (SIDS). Smartbit components can be modularly encased electronics in steel and be designed to conform with horsebit designed. Furthermore, for example, one or more sensors/biosensors can be integrated in one or more PCB designed to include one or more sensors in the oral cavity. This sensor network can communicate with other sensors/biosensors; touching, in proximity, on or internal to an animal's body or human's body. In addition, an orally based accelerometer(s), gyroscope(s), GPS, GPRS and other measurement sensors and technologies can be integrated and networked.

One embodiment of the present invention can use embedded or attached micro cameras and other technologies to identify the tongue, mouth, cheek, teeth and oral cavity. In other words, the embedded camera, for example can provide one or more images of the tongue and other parts of the oral cavity to identify the horse or human. These unique oral identifiers ("oralprints" IDs) can be used synonymous to in similar manner to other bio-identifiers such as "fingerprints" {facial recognition, pupil and eye identification, etc. . . . }

The embedded or attached mouth device includes a non-implanted transmitter which communicates to a radio receiver, smartphone or other device capable of displaying one or more measurements. In addition, the wireless bio-sensor can be attached or embedded to the smartbit including but not limited to a horse-bit, upper mouth smart retainer, the lower mouth smart retainer and both lower and upper when required or other orally placements or attached placements near the oral cavity.

In addition, the smart retainer could, include a multitude of other biosensors and electronics which could measure SpO2, blood oxygen, temperature, pulse, blood pressure, and other biometrics measurements and technologies. Other physiological biometric analysis can help the medical industry with a multilayered health composite and analytic data to measure the changes in an animal's or human's metabolism, drug identification and metabolic reactions to drugs.

In one embodiment of the present invention, the equine smartbit with embedded biosensors can measure various legal and illegal medication, significant pharmacological effect and thresholds. The invention can be used to measure thresholds which meet ARCI standards and relay the data and identification of the horse securely in real-time or near-time to ARCI officials.

In addition in another embodiment, an animal's or human's saliva can be tested for various health related issues through the smartbit. The wireless equine smartbit or smart mouth device for example, can diagnose an animal or human's saliva and biometrics to test drugs, combination of drugs and the changes in metabolism through one or more sensors.

In addition, the electronic receiver wearables (smart oral or body worn devices) whether for animals or humans can update new levels with nearly continuous updates, alerting status when outside the normal set-points and new information regarding new counter measures and technology to detect various drugs recently discovered for example.

In a different embodiment, software application for owners, trainers, jockeys, veterinarians and others associated with the horse can register the animals and monitor biometric, trends and analytics. This can include biometric trends and analytics resulting from drug usage.

In a further embodiment of the invention for example, the software program can send data and alert racing authorities to changes (physiological and metabolic) do to various substances; i.e., drugs and feed.

In another embodiment of the system and software enables a plurality of various data to be transmitted and remotely analyzed such as the identification of the horse through the embedded smartbit camera, saliva and other unique identifiers will identify the horse, transmit the digital images and identification match, transmit information regarding doping and drugs tested in saliva, transmit the animal's metabolic effects and other information.

In another different embodiment of the invention, a registration of a horse's bio-identification using the mouth can be in the form of the unique biomarkers in saliva, biometric identifiers through one or more sensors placed in the mouth and various images (high-definition photos, IR or other images) which identify the horse through the distinctions of the inner mouth.

The secure wireless transmission and identifiers based on the initial equine registration process will be transmitted or submitted to one or more governing organizations and logged in a secure database. In this manner, subsequent doping and drug tests and results are analyzed and accompanied by these unique identifiers to make sure it's the same registered horse and not circumvented.

Another embodiment of the invention includes manually requested spot checks using the SIDS system. The SIDS software will identify the horse as described above, match the horse's ID with prior logs and conduct real-time/near-time testing. In other words, the SIDS master database and command center will activate various testing modules embedded into the smartbit at various times before the racing event to compare readings, data and analytics for various illegal or legal drugs.

Another embodiment of the invention includes in-vitro biometric measurements using saliva modules, and the electronic sensors and drug testing modules which can be interchangeable to test various drugs. These Momentary Saliva-based Biologics Measurements (MSBM) includes a saliva swab, strip, tester, gatherer, made of various materials can be inserted into the horse's mouth to gather saliva as well as direct biometric data. The MSBM electronic device can either transmit the data and the horse's identification or physically gather the data for a more intensive laboratory investigation. Both equine devices (SIDS and MSBM) are indicators of various drug use and to flag such usage if illegal to the proper authorities for further testing. The SIDS/MSBM system and toolkit which can be customized to monitor and measure, compare, analyze, a multitude of various measurements and personalized physiological management markers referred to as set points. Set points are defined as a range of optimal or less than optimal conditions.

Another embodiment of the invention includes tamper proof modules embedded into the SIDS and MSBM device. These modules contain various replaceable test strips designed to detect various drugs and new doping chemicals. The test strips modules can be formulated to test one or more drugs through the animal's saliva. The chemical reaction then monitored by the SIDS and MSBM sensors. Furthermore, the sensors can be modulated as well as interchangeable to detect, measure and monitor new performance enhancing drugs or existing drug usage, medical condition i.e. blood pressure, glucose levels, saliva based glucose testing, pulse, SPO2 etc. It is understood that the smartbit device can be used as a smart-mouthguard and smart retainer etc., for drug testing and health testing and diagnosis for humans and other animals.

DETAILED DESCRIPTION OF THE DRAWINGS

The foregoing summary, as well as the following detailed description of certain embodiments will be better understood when read in conjunction with the appended drawings. As used herein, an element or step recited in the singular and proceeded with the word "a" or "an" should be understood as not excluding the plural of said elements or steps, unless such exclusion is explicitly stated. Furthermore, references to "one embodiment" or "an embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

As used herein, the term "smart" means a device or object that performs one or more functions of a computer or information system, such as data storage, calculation, internet access and information transmission.

As used herein the terms "insertable", "implantable", "imbeddable", "embeddable", "temporarily insertable" "permanently insertable", "temporarily implantable", "permanently implantable", "temporarily imbeddable", "permanently imbeddable", "temporarily embeddable" and "permanently embeddable" refer to means of securely inserting and attaching in or to, or fastening a device, such as being adhered to, cemented, affixed or otherwise securely attached to a surface or object.

Figure 1:
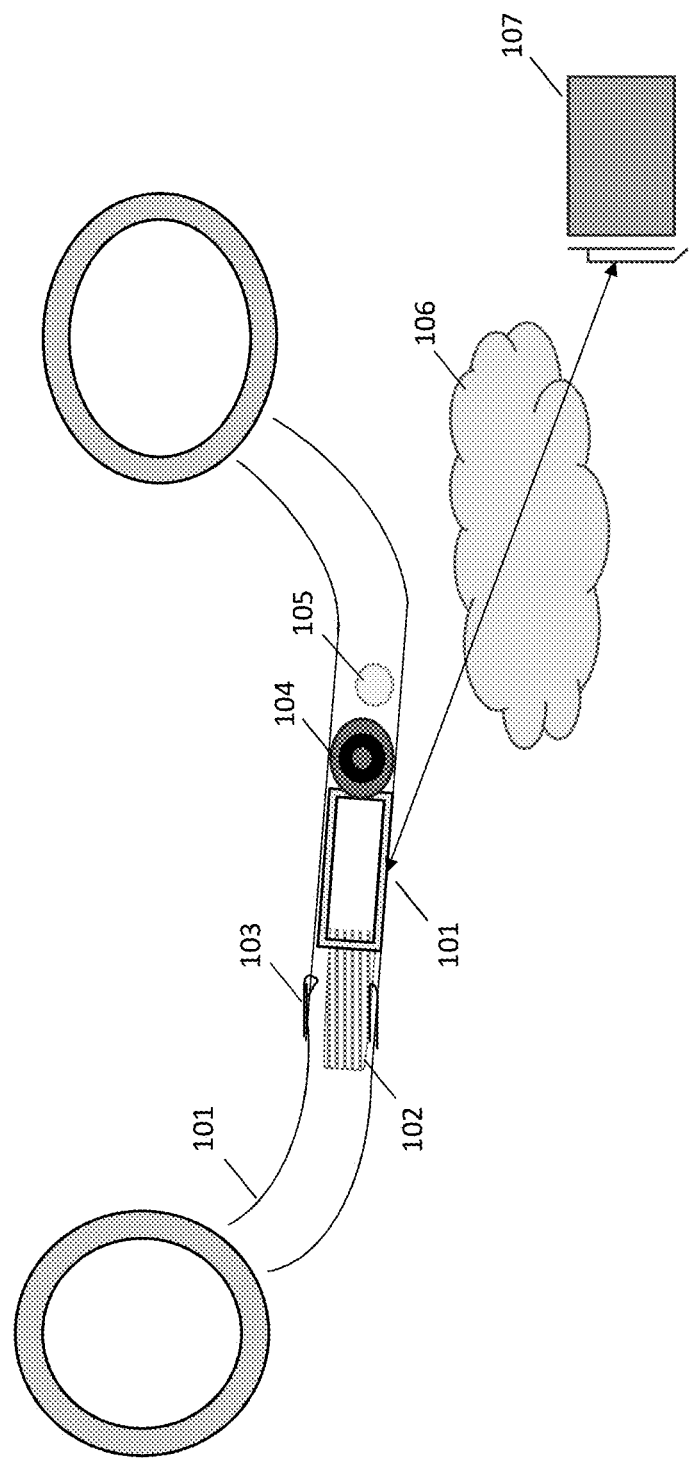
FIG. 1 shows an example of components of the a smart horsebit and SIDS/MSBM device and API in one or more embodiments of the present invention.
Figure 2:
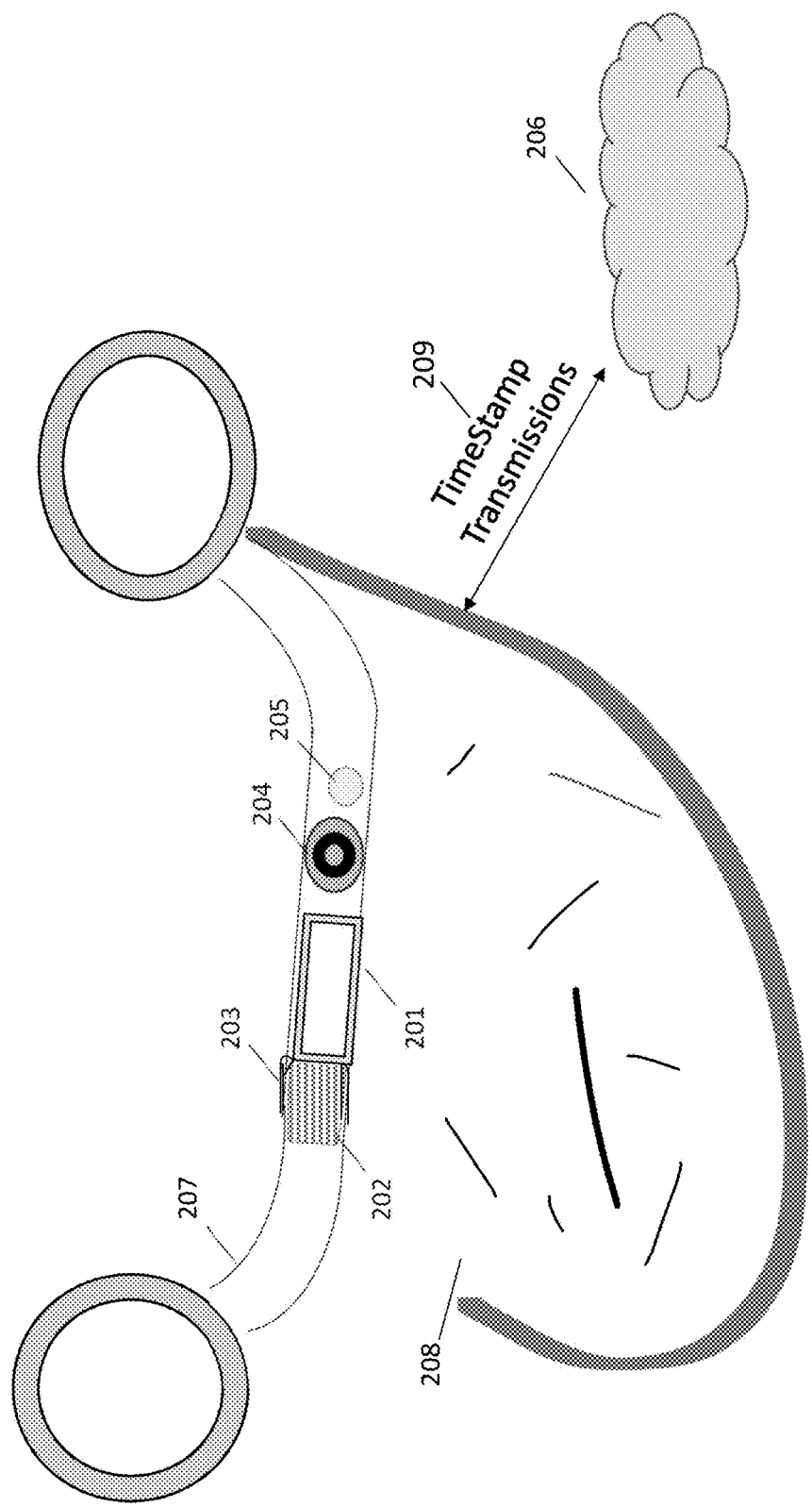
FIG. 2 shows an example of oral-based identification system in conjunction with an embedded smart horsebit biometric measurements in one or more embodiments of the present invention.

FIG. 1 is an example of a Smartbit ID System (SIDS/MSBM) which can include any embedded or attached unit such as but not limited to a mouth retainer, sports guard, sleeve, adhesive, sleeved, denture etc. In this example, a horsebit is make smart by including a modular embedded device 101 where various sensors are embedded which can test a horse's metabolism and changes in physicality. Various test strips module for drug testing exemplified by 102. The test strips are interchangeable and can be replaced by a plurality of various modules designed to test and detect current and new performance enhancing drugs in the equine sports industry. The problem of first identifying the horse becomes a critical step. This 104 represents a camera which takes a picture of the horse's mouth prior to testing the animal for drugs. 105 represents a light which is used in conjunction with the photo. 106 represents a secure API and database which receives biometric and drug testing information. The wirelessly transmitted information is then analyzed by drug testing laboratories which reads the encrypted data and interprets the data to test the use of various drugs. In addition, the SIDS system can unitarily work independently to test various types of drugs or in conjunction with drug testing labs 107. 103 represents a secure modular capsule which contains various drug testing unit. The module unit can be interchangeable, updated and interchangeable to test one or more drugs and their reactions to saliva in the mouth. The module is locked in order to prevent tampering. 101 simultaneous FIG. 2 Oral cavity much like a "fingerprint" is unique and can identify unique features of the mouth (tongue, cheek, teeth etc.) as represented by 208. The ability to take a high-definition photo of various parts of the animal's mouth provide a unique identifier to each animal and positive timestamp 209 proof of both ID and the drug test, medical health and data transmission in real-time/near-time through wireless transmitters 209 and the SIDS/MSBM 207 system and network. Thus, this symbiotic relationship application specific integration of timestamping 209, identification (204/205), biosensors 201, electronics applications, software, drug/health testing 202 technologies and secure wireless networks 206 creates an effective toolkit for the treatment of animals and humans.

Figure 3:
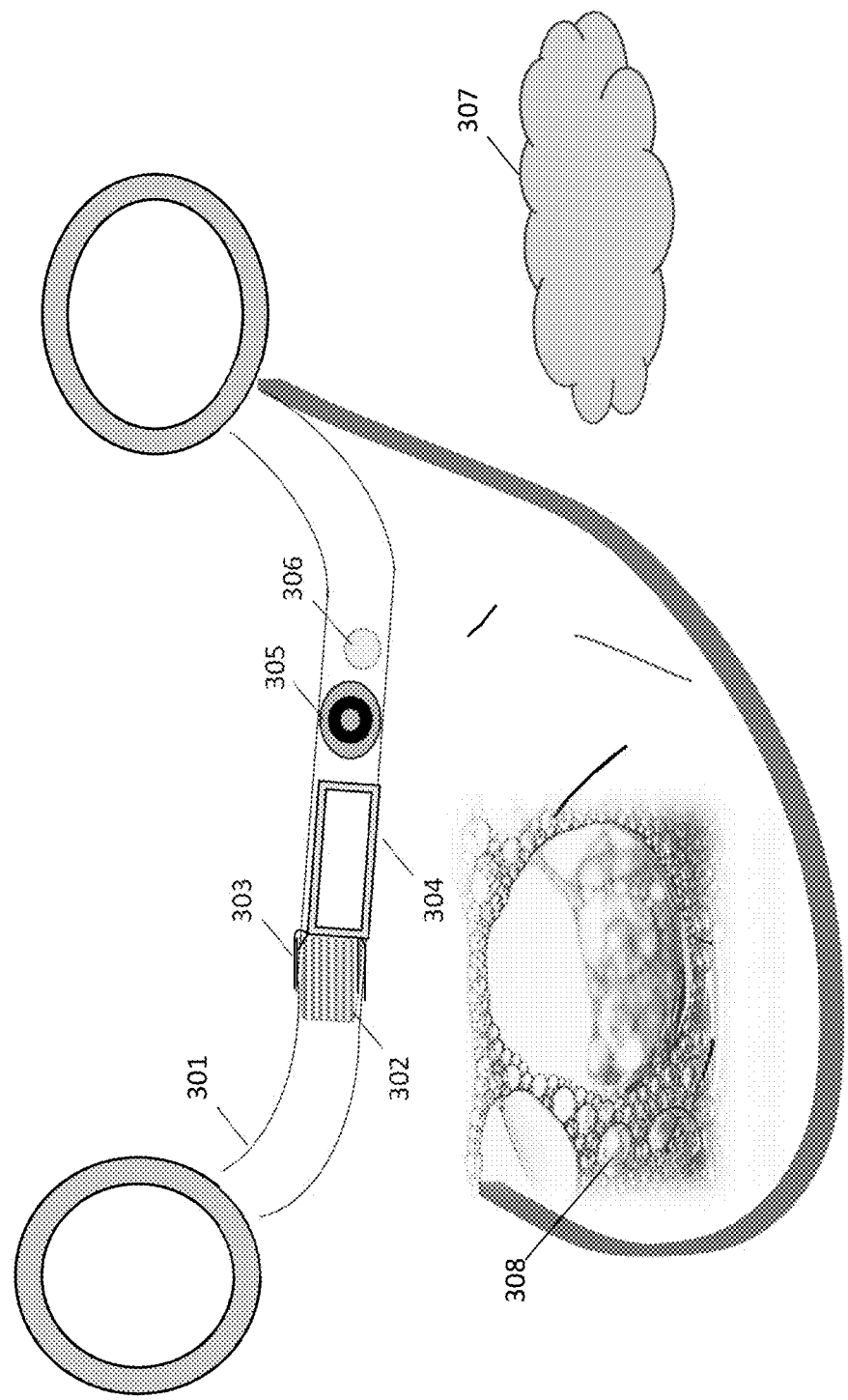
FIG. 3 shows an example of the drug testing modules and chemical reaction saliva and drugs sensors in one or more embodiments of the present invention.

FIG. 3 shows an example of a saliva 308 and oral cavity drug and health (glucose etc.) monitoring unit which can synergistically work with other ancillary biosensors and biometric measurements 304 such as but not limited to Spo2 levels, pulse, temperature and other biometrics as it relates to a network of worn biometric sensors 304. In addition, 305/306 as previously prescribed can be used to identify the patient whether animal or human when testing saliva and health through the SIDS/MSBM diagnostic system. Serving to identify a disease and health condition and indicators. Diagnostics is the art or practice of medical diagnosis. The SIDS/MSBM device 301 and system can detect symptoms and distinguishing features serving as supporting evidence in a for the use of legal and illegal drugs in humans and animals. As previously described the SIDS/MSBM system can be in the form of any oral device i.e., a smart retainer or smart mouthguard, etc. for humans. The invention's SIDS/MSBM device is an instrument or a technique used for medical diagnosis and fast notification and alerting if problems exists. In addition, a secure API based cloud network 307 could provide real-time, near-time and historical time-stamped logs, trend analysis, reporting, alerting notifications, drug and health biosensors 302 and other analytics through a secure network. Monitoring health diagnostics and medical conditions can be described by another embodiment, for example, blood sugar concentration or blood glucose level is the amount of glucose (sugar) present in the blood of a human or animal and monitored using saliva in conjunction with the SIDS/MSBM glucose sensor device, testing strips i.e., multilayers of graphene petals. Furthermore, for example the element (Pt) is combined with nanoparticles (NPs), polyaniline (PANI), glucose oxidase (Gox), and nafion PtNP are electrodeposited into the graphene for its catalytic properties toward hydrogen peroxide in a process which is generated in the process of glucose oxidase (Gox) oxidizing glucose acts as an electron-transfer promoter. Graphene petals were developed by Purdue University. However, an oral monitoring device SIDS/MSBM as previously described can embedded one or more biosensors which can monitor glucose levels and glucose sensitivity in humans and animals through the oral cavity and the chemical relation when exposed to saliva. The SIDS/MSBM device can provide a flexible and strong monitoring system for a multitude of various human and animal medical and physiological conditions designed for the oral cavity and saliva testing in addition to drug testing sensors and biosensors. The SIDS and MSBM can utilize a wide variety of application specific circuitry and designs, requirements to effective monitor a plurality of biomedical applications through these low power transmitters and wireless networks.

Figure 4:
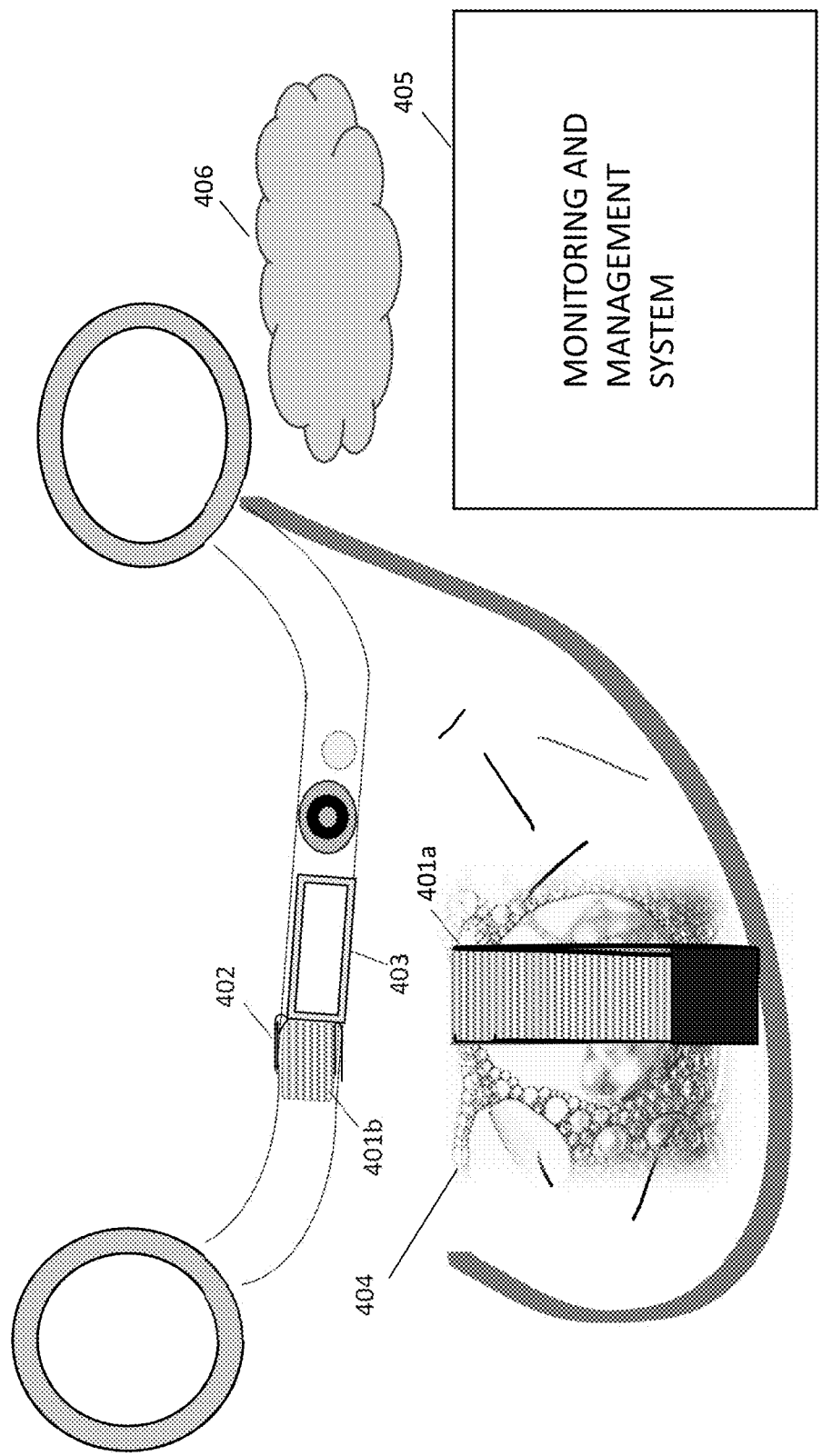
FIG. 4 shows an example of a digital drug test strip device and module (MSBM) in one or more embodiments of the present invention.

FIG. 4 shows an example of a MSBM 401a device which is temporarily inserted into the oral cavity for a human and animal. The historical mobile based app and internet based dashboard and monitoring management system represented by 405 for saliva based biologics and other biometric measurements and dynamic testing modules 401b will wirelessly transmit health information and drug doping information as a non-invasive spot check. The drug testing modules 401*b* can contain one or more catalysts or reactants designed for various physiological health. 401*a* and 401*b* exemplifies an interchangeable modules which are specifically designed to react to saliva and its reaction(s) both physically and chemically diagnosed through a network of biosensors (403). In addition, the secure API and database 406 could filter logic, artificial intelligence and one or more physiological devices which connect, communicates, and compares a plurality of timestamp results stemming from consumed foods, physiological health, drugs, sleep, exertion, stress and other environmental factors. In addition, biometric measurements which are communicated to the patient through one or more networks and mobile devices.

As described herein, some embodiments of the present invention might be implemented as a software application downloadable to a mobile device. The downloaded software application might work with existing hardware of the mobile device to implement an emergency notification alert system as described herein. For example, some embodiments might be available as an "app" or icon on the screen of the mobile device. Alternatively, some embodiments of the present invention might require special purpose hardware, and this might only be compatible with mobile devices having the emergency notification hardware.

Reference herein to "one embodiment" or "an embodiment" means that a feature, structure, or characteristic described in conjunction with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

While the exemplary embodiments of the present invention have been described with respect to processing blocks in a software program, including possible implementation as a digital signal processor, micro-controller, or general purpose computer, the present invention is not so limited. As would be apparent to one skilled in the art, various functions of software may also be implemented as processes of circuits. Such circuits may be employed in, for example, a single integrated circuit, a multi-chip module, a single card, or a multi-card circuit pack.

The present invention can be embodied in the form of methods and apparatuses for practicing those methods. The present invention can also be embodied in the form of program code embodied in tangible media, such as magnetic recording media, optical recording media, solid state memory, floppy diskettes, CD-ROMs, hard drives, or any other machine-readable storage medium, wherein, when the program code is loaded into and executed by a machine, such as a computer, the machine becomes an apparatus for practicing the invention. The present invention can also be embodied in the form of program code, for example, whether stored in a transmission medium or carrier, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits. The present invention can also be embodied in the form of a bitstream or other sequence of signal values electrically or optically transmitted through a medium, stored magnetic-field variations in a magnetic recording medium, etc., generated using a method and/or an apparatus of the present invention.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

The invention claimed is:

1. A sensor arrangement for use during a competition, comprising:
    an oral cavity-based device configured for placement in an oral cavity of a horse;
    a biosensor receptacle affixed to the oral cavity-based device;
    one or more biosensors that are received in the biosensor receptacle, wherein the biosensor receptacle is locked when placed in the oral cavity such that the biosensor is irremovable during the competition; and
    a processor, a memory, and a transmitter that are in communication with the biosensor receptacle.

2. The sensor arrangement of claim 1, wherein the transmitter is in communication with the processor.

3. The sensor arrangement of claim 2, wherein the transmitter is configured to transmit data from the processor to a receiver or computing device; wherein data transmitted from the processor to the receiver or computing device includes data from the one or more biosensors.

4. The sensor arrangement of claim 3, wherein the processor is configured to transmit data continuously in real time or at near real-time to the receiver or the computing device.

5. The sensor arrangement of claim 3, wherein the transmitter is configured to transmit data from the processor to the receiver or computing device of a horse racing authority when data is outside normal set-points.

6. The sensor arrangement of claim 2, wherein the biosensors measure one or more pharmaceutical in saliva of the horse.

7. The sensor arrangement of claim 1, wherein the oral cavity-based device further comprises a camera engaged to the oral cavity-based device and disposed within the oral cavity during use and the camera is configured to transmit data to the processor.

8. The sensor arrangement of claim 7, wherein the camera captures one or more images of the oral cavity, wherein the camera generates an oral print ID comprising captured images the horse's oral cavity.

9. The sensor arrangement of claim 8, wherein the oral-print ID further comprises a unique identifier of the oral cavity based on structural features of the oral cavity, and wherein the oralprint ID includes a positive timestamp.

10. The sensor arrangement of claim 8, wherein the oral cavity-based device further comprises a light that is engaged to the biosensor receptacle, wherein the light is configured to light the oral-cavity when capturing the one or more images.

11. The sensor arrangement of claim 1 wherein the biosensors further comprise one or more test strips that are received in the biosensor receptacle and configured to identify one or more substances in saliva of the horse.

12. The sensor arrangement of claim 1 wherein the oral cavity-based device is configured as a bit.

13. The sensor arrangement of claim 1, wherein the biosensor receptacle and the one or more biosensors are tamper proof.

14. A method of non-invasive monitoring using a sensor arrangement comprising an oral cavity-based device having a biosensor receptacle and one or more biosensors that are received in the biosensor receptacle, wherein the one or more biosensors are configured to be removeable from the biosensor receptacle; the oral cavity-based device configured for placement in an oral cavity of an equine mammal and further comprising a processor, a memory, and a transmitter in communication with the biosensor receptacle; the method comprising:
- inserting the oral cavity-based device into the oral cavity of the equine mammal;
- inserting and locking the one or more biosensors in the biosensor receptacle;
- contacting the one or more biosensors with saliva from the equine mammal; and
- identifying components of the saliva using the one or more biosensors and transmitting data responsive thereto.

15. A sensor arrangement for use during a competition, comprising:
- an oral cavity-based device configured for placement in an oral cavity of a horse;
- a biosensor receptacle affixed to the oral cavity-based device;
- one or more removable biosensors that are received in the biosensor receptacle, wherein the biosensor receptacle is locked when placed in the oral cavity such that the biosensor is irremovable during the competition;
- a camera engaged to the oral cavity-based device and disposed within the oral cavity during use;
- a processor;
- a memory; and
- a transmitter configured to communicate with the biosensor receptacle, the processor, the camera, and a receiver configured to display data from at least one of the processor, the camera, or the memory.

* * * * *